United States Patent [19]

Davidson

[11] 3,954,992

[45] May 4, 1976

[54] 2-CYANO-2-HYDROXYIMINOACETAMIDES AS PLANT DISEASE CONTROL AGENTS

[75] Inventor: Sidney Hayes Davidson, Wilmington, Del.

[73] Assignee: E. I. Du Pont de Nemours and Company, Wilmington, Del.

[22] Filed: Mar. 21, 1974

[21] Appl. No.: 453,392

Related U.S. Application Data

[63] Continuation-in-part of Ser. No. 375,376, July 2, 1973, abandoned, which is a continuation-in-part of Ser. No. 330,457, Feb. 7, 1973, abandoned, which is a continuation-in-part of Ser. No. 234,997, March 15, 1972, abandoned.

[52] U.S. Cl. .................... 424/287; 424/141; 424/164; 424/246; 424/DIG. 8; 424/249; 424/273; 424/274; 424/286; 424/288; 424/289; 424/295; 424/300; 424/304; 424/319; 424/321; 424/329; 260/465 D; 260/465.4

[51] Int. Cl.² ..................... A01N 19/00; A01N 9/06

[58] Field of Search .......... 424/304, 141, 164, 246, 424/249, 273, 274, 286, 287, 300, 329

[56] References Cited

UNITED STATES PATENTS

3,625,987  12/1971  Hubele ........................... 424/244

OTHER PUBLICATIONS

Berichte, 42 (1909), pp. 738–742, Conrad et al.
Berichte, 54 (1921), pp. 1342–1343, Diels et al.

*Primary Examiner*—V. D. Turner

[57] ABSTRACT

Compounds of the formula

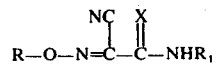

such as 2-cyano-2-hydroxyiminoacetamide and 2-cyano-N-ethylcarbamoyl-2-methoxyiminoacetamide are useful in preventing fungus diseases in plants.

27 Claims, No Drawings

2-CYANO-2-HYDROXYIMINOACETAMIDES AS PLANT DISEASE CONTROL AGENTS

CROSS REFERENCE TO RELATED APPLICATIONS

This application is a continuation-in-part of copending application Ser. No. 375,376, filed July 2, 1973, now abandoned, which is a continuation-in-part of copending application Ser. No. 330,457, filed Feb. 7, 1973, now abandoned, which is a continuation-in-part of application Ser. No. 234,997, filed Mar. 15, 1972, now abandoned.

BACKGROUND OF THE INVENTION

This invention relates to a class of compounds which are useful in controlling diseases of plants. Fungi and other disease incitants cause extensive losses in crops annually. While there are commercially available materials effective in preventing many plant diseases, still further improvement in this art is needed if full food and fiber production is to be realized. The compounds of this invention are particularly effective for the control of fungus plant diseases like potato and tomato late blight as well as the downy mildews. In addition, most of the compounds of this invention exhibit systemic and curative properties. Relatively small amounts of material can be used to eradicate or cure existing plant disease caused by fungi. This is in contrast to most conventional protective materials which must be applied in advance of attack.

SUMMARY OF THE INVENTION

Compounds of the formula

(I)

wherein
R is hydrogen; alkyl of 1 to 13 carbon atoms; alkyl of 1 to 13 carbon atoms substituted with alkoxycarbonyl of 2 to 4 carbon atoms, acyl of 2 to 4 carbon atoms, cyano, hydroxyl, acyloxy of 2 to 4 carbon atoms.

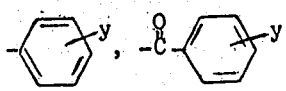

or

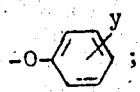

alkenyl of 3 to 6 carbon atoms; cycloalkyl of 5 to 7 carbon atoms;
O,O-dialkylthiophosphoryl of 2 to 4 carbon atoms; acyl of 1 to 4 carbon atoms;

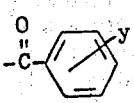

or a cation selected from the group consisting of lithium, sodium, potassium, iron, calcium, zinc, manganese, or $NR_2R_3R_4R_5$;

y is hydrogen, chlorine, fluorine, bromine, methyl or cyano;
$R_2$ is hydrogen, alkyl of 1 to 4 carbon atoms, 2-hydroxyethyl or alkoxyethyl of 3 to 4 carbon atoms;
$R_3$ is hydrogen, alkyl of 1 to 4 carbon atoms, 2-hydroxyethyl or alkoxyethyl of 3 to 4 carbon atoms, or $R_2$ and $R_3$ taken together can form a pyrrolidino, piperidino, morpholino or hexahydroazepino ring;
$R_4$ is hydrogen, alkyl of 1 to 4 carbon atoms, 2-hydroxyethyl, or alkoxyethyl of 3 to 4 carbon atoms;
$R_5$ is hydrogen, alkyl of 1 to 12 carbon atoms, 2-hydroxyethyl, alkoxyethyl of 3 to 4 carbon atoms or benzyl;
$R_1$ is hydrogen,

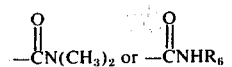

$R_6$ is hydrogen, alkyl of 1 to 4 carbon atoms or allyl;
X is oxygen or sulfur with the proviso that
1. when $R_1$ is

or when X is sulfur, R is methyl;
2. when R is a cation, $R_1$ is hydrogen;
3. when R is substituted alkyl, the total number of carbon atoms in R is less than 14;

are useful in controlling diseases of plants. Application of these compounds to the locus to be protected from disease effectively prevents the debility. Most of these compounds are also systemic and curative in plants. Because they are curative, the compounds can be applied before or after the plants to be protected are infected by fungi. This curative activity makes the compounds of this invention particularly valuable for combination and application with conventional fungicides. Because the compounds are systemic in plants, the compounds can be applied not only directly to the infected plant parts, but also to uninfected parts of the plant or to the soil. All of these application sites are included within the term "applying to the plants".

For each of the compounds described above, there are two geometric isomers. Of the compounds described above, those are novel wherein
R is alkyl of 1 to 13 carbon atoms; alkyl of 1 to 13 carbon atoms substituted with alkoxycarbonyl of 2 to 4 carbon atoms, acyl of 2 to 4 carbon atoms, hydroxyl, cyano, acyloxy of 2 to 4 carbon atoms,

alkenyl of 3 to 6 carbon atoms; cycloalkyl of 5 to 7 carbon atoms; O,O-dialkylthiophosphoryl of 2 to 4 carbon atoms; acyl of 1 to 4 carbon atoms;
or

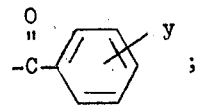

$R_1$ is

and $R_6$ and y are defined as above. Within the novel compound scope, those where $R_6$ is hydrogen or alkyl of 1 to 4 carbon atoms are preferred.

Within the broad scope, preferred are those compounds where $R_6$ is hydrogen or alkyl of 1 to 4 carbon atoms, provided that when R is alkyl of 2 to 6 carbon atoms or cycloalkyl of 5 to 7 carbon atoms, $R_1$ is

Of the compounds described, those preferred for reasons of high activity and economy are compounds of the formula

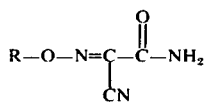

wherein

R is hydrogen, methyl or a cation, more preferably, wherein R is hydrogen or a cation as defined above and compounds of the formula

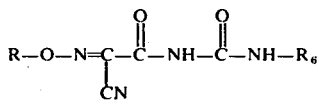

wherein R is alkyl of 1 to 4 carbon atoms and $R_6$ is hydrogen, alkyl of 1 to 4 carbon atoms and allyl. Specifically preferred for very high activity and economy are 2-cyano-2-hydroxyiminoacetamide, 2-cyano-2-hydroxyiminoacetamide, sodium salt; 2-cyano-2-hydroxyiminoacetamide, ammonium salt; 2-cyano-2-methoxyimino-N-methylcarbamoylacetamide; N-carbamoyl-2-cyano-2-methoxyiminoacetamide; 2-cyano-N-ethylcarbamoyl-2-methoxyiminoacetamide; 2-cyano-2-ethoxyimino-N-ethylcarbamoylacetamide; N-allylcarbamoyl-2-cyano-2-methoxyiminoacetamide; 2-cyano-2-methoxyimino-N-propylcarbamoylacetamide.

Effective compositions of the compounds described above consist essentially of one of the above compounds and an inert diluent. Surfactants can also be included as well as other ingredients which do not detract from the effectiveness of the active compound.

DETAILED DESCRIPTION OF THE INVENTION

The compounds useful in this invention are in part known and can be made as described in the literature or by known methods.

2-Cyano-2-hydroxyiminoacetamide

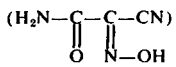

can be made by nitrosation of cyanoacetamide with sodium nitrite and acetic acid as described by M. Conrad and A. Schulze, Ber. 42, 738 (1909). The compound may also be prepared from the corresponding hydroxamyl chloride and an alkali or alkaline earth cyanide, for example in the following manner.

A solution of 50 grams of 2-chloro-2-hydroxyiminoacetamide in 200 ml. of methanol was added over 2 hours to a solution of 40 grams of sodium cyanide in 160 ml. of water at 0°–5°C. The methanol was removed on a rotary evaporator and 200 ml. of water was added to the residue. The solution of the sodium salt of 2-cyano-2-hydroxyiminoacetamide thus obtained was adjusted to pH 2.5 at 0°–5°C. with concentrated hydrochloric acid. The solid was collected by filtration to give 31 grams 2-cyano-2-hydroxyiminoacetamide, m.p. 180°–182°.

2-Cyano-2-hydroxyiminoacetamide was prepared also by the following procedure: To a solution of 49 grams of 2-chloro-2-hydroxyiminoacetamide in 200 ml. of methanol at 0°C. was added 19 grams of hydrogen cyanide, followed by 38 grams of 50% sodium hydroxide over a period of 2 hrs. The methanol was removed on a rotary evaporator and water was added to the residue. The solution of the sodium salt thus obtained was adjusted to pH 2.5 at 0°–5°C. with concentrated hydrochloric acid. The solid was collected by filtration to give 2-cyano-2-hydroxyiminoacetamide.

Salts of 2-cyano-2-hydroxyiminoacetamide can be made in various ways. For example, the sodium salt can be isolated from the above-described reactions prior to the acidification step. Salts can be made from the free oxime by slurrying the free oxime in water, adding an aqueous solution of an equivalent amount of the appropriate base such as sodium, calcium, potassium or ammonium hydroxide, warming the mixture until the solid is dissolved, and vaccum concentrating the solution. Relatively insoluble salts such as the zinc and manganese salts can be made by adding an equivalent amount of the appropriate heavy metal salt to an aqueous solution of a soluble salt such as the sodium salt, and collecting the insoluble salt by filtration.

When prepared as described above, some of the salts are obtained in the form of hydrates, which are perfectly suitable as such for fungicidal application. In fact, the solutions of the soluble salts prepared as described above can be used as such for fungicidal application after dilution to the desired spray concentration. As exemplified below, the anhydrous forms can be obtained by drying of the hydrates or by preparing the salts under anhydrous conditions. In some cases, such as the sodium or ammonium salt, the addition of half the required amount of the desired base leads to the precipitation of a 1:1 complex of free oxime and salt which are meant to be included by the claim language. Examples of the salts and complexes follow.

2-Cyano-2-hydroxyiminoacetamide, Sodium Salt

Technical 2-cyano-2-hydroxyiminoacetamide at 96% purity (500 grams) was heated with 750 ml. of water to effect solution. With efficient stirring, 25% aqueous sodium hydroxide was added until a pH of 7.5 was reached (99+% neutralized). The orange solution was cooled and stirred and the yellow sodium salt which slowly precipitated was filtered and rinsed with a little methanol. Additional product was obtained by concentration of the mother liquor. Dried in air it exists as monohydrate; vacuum dried at 45° under nitrogen it loses water to yield anhydrous salt. The calcium salt is similarly prepared but with solid calcium hydroxide and hot filtration to remove traces of calcium carbonate.

2-Cyano-2-hydroxyiminoacetamide, Sodium Salt, Complex with 2-Cyano-2-hydroxyiminoacetamide Technical 2-cyano-2-hydroxyiminoacetamide (58.5 grams) was heated with 100 ml. water to form a solution. With strong stirring, a solution of 19 grams of 50% aqueous sodium hydroxide in 20 ml. water was added. In a few seconds a thick precipitate formed. After cooling the white precipitate was filtered and dried under vacuum to yield 56 grams of anhydrous complex salt.

2-Cyano-2-hydroxyiminoacetamide, Lithium Salt

To 35 ml. of water, 30.4 grams of technical 2-cyano-2-hydroxyiminoacetamide was added concurrently with saturated lithium hydroxide maintaining the pH at about 7 (i.e., slight deficiency of base). The material was then filtered to clarity, the water evaporated and the residue triturated with methanol to remove unneutralized material and vacuum dried to produce anhydrous lithium salt.

2-Cyano-2-hydroxyiminoacetamide, Ammonium Salt

A solution of 175.5 grams of 96% purity technical 2-cyano-2-hydroxyiminoacetamide in 800 ml. of methanol was filtered to clarity. With rapid stirring 105 ml. of commercial aqueous ammonia (5% excess) was added. After a short time crystals of the yellow ammonium salt hydrate began to precipitate and were collected by filtration. Additional product is obtained by concentration of the mother liquor.

2-Cyano-2-hydroxyiminoacetamide, Ammonium Salt Complex with 2-Cyano-2-hydroxyiminoacetamide The reaction described above was carried out exactly as described except that only 50 ml. of aqueous ammonia was added. The precipitate was practically white and titration with standardized ammonia in water confirmed the identity of the complex salt. The same complex was obtained by allowing the ammonium salt to stand open to the atmosphere for an extended period.

2-Cyano-2-hydroxyiminoacetamide, Manganese Salt

To a solution of 45.2 grams of 2-cyano-2-hydroxyiminoacetamide in 100 ml. 4 N NaOH was added dropwise with stirring a solution of 43.5 grams of $MnCl_2 \cdot 4 H_2O$ in 50 ml. of water. The resulting slurry was cooled in ice, filtered and washed thoroughly with ice water and dried in a stream of air at room temperature. The manganese salt thus prepared contains about 27% water and is perfectly suitable as such for fungicidal application. The amount of water can be reduced by slurrying in a suitable water-miscible solvent such as acetone and filtering, or by vaccum drying at elevated temperatures.

2-Cyano-2-hydroxyiminoacetamide, Zinc Salt

To a solution of 45.2 grams of 2-cyano-2-hydroxyiminoacetamide in 400 ml. 1 N NaOH was added dropwise with stirring a solution of 30 grams of zinc chloride in 100 ml. water. The light yellow precipitate was collected on a filter, washed thoroughly with water and acetone, and dried in a stream of air at room temperature. The zinc salt thus prepared contains some water and some zinc oxide but is perfectly suitable for fungicidal use. The amount of zinc oxide formed can be reduced by carrying out the above precipitation by simultaneous addition of the two starting solutions to agitated water under controlled pH conditions.

2-Cyano-2-hydroxyiminoacetamide, Ferric Salt

A solution of 3.3 grams of ferric chloride hexahydrate in 400 ml. water was added to a solution of 4.0 grams of 2-cyano-2-hydroxyiminoacetamide in 35 ml. 1 N sodium hydroxide diluted to 500 ml. The resulting brown solution was diluted with water to a total volume of 1 liter. The solution thus obtained contained 4,000 ppm of the desired ferric salt and was used as such for preparing the proper dilutions required for fungicidal spraying.

Other Salts of 2-Cyano-2-hydroxyiminoacetamide

Using the same general procedure as described above, e.g. dissolving 2-cyano-2-hydroxyiminoacetamide in an aqueous solution of an equivalent amount of the appropriate base and vacuum concentrating the solution, the salts listed in the following table are made:

| 2-Cyano-2-hydroxyimino-acetamide | potassium | salt |
|---|---|---|
| " | dimethylammonium | " |
| " | propylammonium | " |
| " | tributylammonium | " |
| " | triethanolammonium | " |
| " | methoxyethylammonium | " |
| " | dodecylammonium | " |
| " | benzylammonium | " |
| " | ethoxyethylammonium | " |
| " | pyrrolidinium | " |
| " | piperidinium | " |
| " | morpholinium | " |
| " | hexahydroazepinium | " |

2-Cyano-2-methoxyiminoacetamide $$(H_2N-\underset{\underset{O}{\|}}{C}-\underset{\underset{N-OCH_3}{\|}}{C}-CN)$$

can be prepared by methylation of 2-cyano-2-hydroxyiminoacetamide (see above) with dimethyl sulfate and aqueous potassium hydroxide as described by O. Diels and E. Borgwardt, Ber. 54, 1342 (1921). The higher alkoxyimino homologs can be conveniently prepared by alkylating the sodium salt of 2-cyano-2-hydroxyiminoacetamide with the appropriate alkyl halide in DMF. For example, 2-cyano-2-n-dodecyloxyiminoacetamide

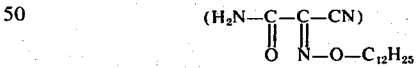

mp 84°–6°, was prepared by dissolving the sodium salt of 2-cyano-2-hydroxyiminoacetamide in dimethylformamide. While stirring, 1-iodododecane was added and the solution heated on the steam bath for six hours. After cooling to room temperature, the solution was poured into water and the precipitate collected on a filter, washed with water and dried.

Other alkyl derivatives, listed in the following table, were prepared in the same way.

$$H_2N-\underset{\underset{O}{\|}}{C}-\underset{\underset{N-OR}{\|}}{C}-CN$$

| R = | M.P. |
|---|---|
| $C_2H_5$ | 123–5° |
| $n\text{-}C_3H_7$ | 105–7° |

-continued $$H_2N-\underset{\underset{O}{\|}}{C}-\underset{\underset{N-OR}{\|}}{C}-CN$$

| R = | M.P. |
|---|---|
| i-C$_3$H$_7$ | 90–2° |
| n-C$_4$H$_9$ | 89–90° |
| n-C$_5$H$_{11}$ | 87–9° |
| n-C$_6$H$_{13}$ | 88–90° |
| cyclohexyl | 146–8° |
| 2-ethyl hexyl | 47–9° |
| n-C$_7$H$_{15}$ | 79.5–80.5° |
| n-C$_8$H$_{17}$ | 84–6° |
| n-C$_9$H$_{19}$ | 86–7° |
| n-C$_{10}$H$_{21}$ | 86–7° |
| n-C$_{11}$H$_{23}$ | 83–4° |
| n-C$_{13}$H$_{27}$ | 86.7° |

Substituted alkyl derivatives or alkenyl derivatives are made in the same way. The following table lists a number of such materials by way of example.

$$H_2N-\underset{\underset{O}{\|}}{C}-\underset{\underset{N-O-R}{\|}}{C}-CN$$

| R = | M.P. |
|---|---|
| 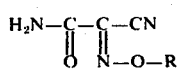 | 88–9° |
| —CH$_2$—CH$_2$—CH$_2$—CN | 77–80° |
| —CH$_2$—COOC$_2$H$_5$ | 143.5–44° |
| 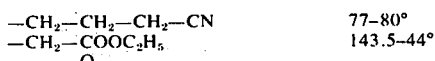 | 120–1° |
|  | 90–1° |
| 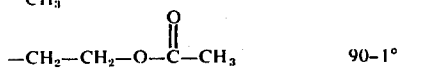 | 146–7° |
| —CH$_2$—CH=CH$_2$ | 78–9° |
| —CH$_2$—CH$_2$—OH | 124–5° |
|  | 180–1° |
|  | 165–5.5° |
|  | 106–7° |
|  | 188–9.5° |
|  | 187–188.5° |
|  | 98–100° |
|  | 139–141° |

-continued $$H_2N-\underset{\underset{O}{\|}}{C}-\underset{\underset{N-O-R}{\|}}{C}-CN$$

| R = | M.P. |
|---|---|
|  —P(OC$_2$H$_5$)$_2$ with ↓S | 110–1° |
|  —C(=O)—CH$_3$ | 143–5° |
|  —C(=O)—C$_6$H$_5$ | 222–3° |
| —P(OCH$_3$)$_2$ with ↓S | — |
| —CH$_2$—CH$_2$—O—C(=O)—CH$_2$—CH$_2$—CH$_3$ | — |
| (CH$_2$)$_2$COC$_3$H$_7$ | — |
| CH$_2$—C(=O)—CH$_3$ | — |
|  CH—C(=O)—(CH$_2$)$_2$—CH$_3$ with CH$_3$ | — |
| —C(=O)—H | — |
| (CH$_2$)$_{12}$CN | — |
|  —CH$_2$—C$_6$H$_5$ | — |
|  —(CH$_2$)$_7$—C$_6$H$_4$—Cl | — |
|  —(CH$_2$)$_3$—C$_6$H$_4$—CN | — |
|  —CH$_2$—C$_6$H$_4$—CH$_3$ | — |
|  —CH$_2$—C(=O)—C$_6$H$_4$—Br | — |
| 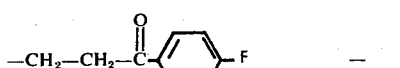 —CH$_2$—C(=O)—C$_6$H$_4$—Cl | — |
| 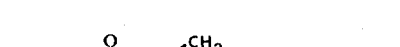 —CH$_2$—CH$_2$—C(=O)—C$_6$H$_4$—F | — |
|  —(CH$_2$)$_3$—C(=O)—C$_6$H$_4$—CH$_3$ | — |
| —(CH$_2$)$_3$—C(=O)—C$_6$H$_4$—CH$_3$ | — |

-continued $$H_2N-\underset{\underset{O}{\|}}{C}-\underset{\underset{N-O-R}{\|}}{C}-CN$$

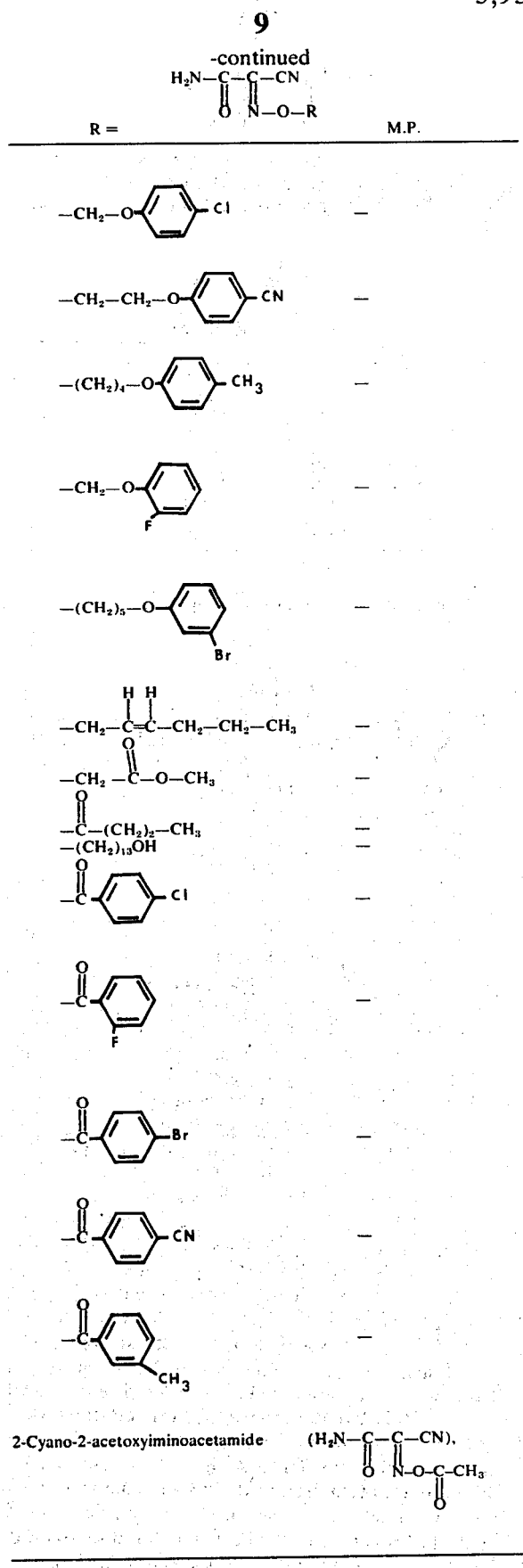

2-Cyano-2-acetoxyiminoacetamide $(H_2N-\underset{\underset{O}{\|}}{C}-\underset{\underset{N-O-\underset{\underset{O}{\|}}{C}-CH_3}{\|}}{C}-CN)$, described by Diels and Borgwardt (see above) is conveniently prepared by introducing ketene gas into a solution of 2-cyano-2-hydroxyiminoacetamide in a suitable solvent such as acetonitrile followed by evaporation of the solvent. The higher acyl analogs can be prepared by reaction of the oxime with the appropriate anhydride, for example propionic anhydride, or with the appropriate acyl chloride, for example n-butyryl chloride, in the presence of a suitable base such as pyridine or triethylamine.

2-Cyano-N-carbamoyl-2-hydroxyiminoacetamide

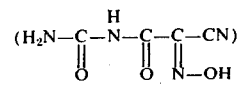

was prepared as described by Conrad and Schulze (Ber. 42, 740-1) from cyanoacetylurea and sodium nitrite followed by acidification. It may also be prepared by the hydroxamyl chloride method described above. Conversion of this compound to the corresponding methoxyimino derivative

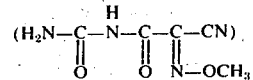

was achieved for example by means of diazomethane in ether and by converting the oxime to the sodium salt with sodium methoxide in dimethyl formamide, adding methyl iodide and stirring the mixture at about 80° for about two hours. This methoxy compound melts at 161°–163°. The latter method was also conveniently used for the preparation of other O-substituted derivatives such as the higher alkyl, substituted alkyl, aralkyl, substituted aralkyl, cycloalkyl, etc. compounds of the above general formula. Examples of such derivatives are listed below.

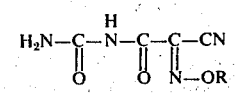

| R = | M.P. |
|---|---|
| —CH$_2$—CH$_3$ | 156.5–7° |
| —CH(CH$_3$)$_2$ | 148–150° |
| —(CH$_2$)$_5$—CH$_3$ | 96–99° |
| 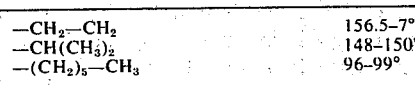 | 178–80° |
| —(CH$_2$)$_{11}$—CH$_3$ | 81–4° |
| —CH$_2$—CH$_2$—CH$_2$—CN | 153–6° |
| —CH$_2$—CH=CH$_2$ | 120–1° |
|  | 152–3° |
| 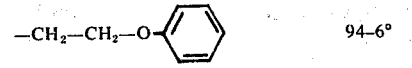 | 94–6° |
|  | 134–6° |
|  | 169–70° |
|  | — |

| R = | M.P. |
|---|---|
|  | — |

2-Cyano-2-methoxyimino-N-methylcarbamoylacetamide

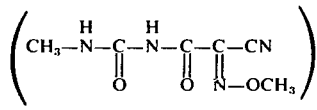

M.P. 176°–7°, was prepared by methylating, with diazomethane in ether, the corresponding free oxime 2-cyano-2-hydroxyimino-N-methylcarbamoylacetamide, the preparation of which is described in German Patent No. 227,390 (Friedlander 10, 1177). This preparation involves the nitrosation of 1-cyanoacetyl-3-methylurea with sodium nitrite in aqueous acetic acid.

The next higher homolog, 2-cyano-N-ethylcarbamoyl-2-methoxyiminoacetamide, M.P. 160°–1°, may be similarly prepared from 1-cyanoacetyl-3-ethylurea and sodium nitrite in aqueous acetic acid or other suitable acid such as hydrochloric acid followed by methylation of the oxime with diazomethane.

This methylation may also be carried out by dissolving the free oxime in dimethylformamide, adding a molar equivalent of a base such as sodium methoxide to convert the free oxime to a salt such as the sodium salt, adding methyl iodide (preferably in excess) and stirring the mixture at room temperature. Methyl bromide may be used instead of methyl iodide. This method is quite suitable also for the preparation of the higher O-alkyl compounds, such as, for example, the propoxyimino derivative.

Another useful method for carrying out the methylation consists in refluxing the free oxime in acetone with powdered potassium carbonate and dimethyl sulfate. The use of a slight excess, for example, 10%, of the latter two reagents increases the yield of the methyl ether. The use of diethyl sulfate in this reaction affords the corresponding ethoxyimino compound.

Yet another suitable method for preparing the ureas of this invention consists in reacting a compound of the general formula

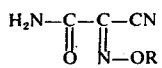

with a suitable base (for example, sodium hydride or sodium methoxide) in order to convert it to the anionic form, and in reacting this anion with an isocyanate of the general formula $R_6$-NCO in a suitable inert solvent such as tetrahydrofuran or acetonitrile, followed by acidification:

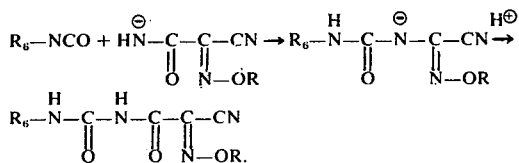

Other homologs of the general formula

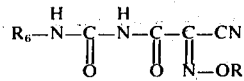

can be made according to the methods described above. Their melting points are listed in the following table.

| $R_6$ = | R = | M.P. |
|---|---|---|
| $C_2H_5$ | $C_2H_5$ | 121–2° |
| $C_2H_5$ | n-$C_3H_7$ | 104–5° |
| $C_2H_5$ | i-$C_3H_7$ | 102–3° |
| $C_2H_5$ | n-$C_6H_{13}$ | 80.5–2° |
| allyl | $CH_3$ | 134–6° |
| n-$C_3H_7$ | $CH_3$ | 121.5–3° |
| i-$C_3H_7$ | $CH_3$ | 137.5–8.5° |
| n-$C_4H_9$ | $CH_3$ | 98–100° |
| sec-$C_4H_9$ | $CH_3$ | 72–3° |
| iso-$C_4H_9$ | $CH_3$ | 108–9° |

2-Cyano-2-hydroxyiminothioacetamide

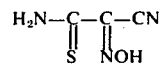

mp 145° dec, was prepared from 2-cyanothioacetamide, sodium nitrite and hydrochloric acid as described by G. Shaw and D. N. Butler, J. Chem. Soc. 1959, 4042. The corresponding methyl ether, 2-cyano-2-methoxyiminothioacetamide

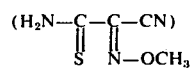

mp 163–5°, was prepared either by methylation of the oxime with dimethylsulfate in aqueous KOH or by reacting 2-cyano-2-methoxyiminoacetamide in a known manner with $P_2S_5$.

Other thiono derivatives such as 2-cyano-2-hydroxyimino-N-ethylcarbamoylacetamide are accessible by means of the above described chemistry and its precursors as well as by means of treatment with $P_2S_5$. As described above, many of the compounds within the scope of this case form hydrates and complexes. Although the claims of this case do not specifically recite the complexes and hydrates, their use and formulations are intended to be within the scope of the claims.

The compounds of this invention are useful as plant disease control agents. Most have qualities of systemic and curative activity when applied to soil, to propagation pieces, to stems, or to foliage. Combinations with other fungicides, especially those with strong residual properties, provide exceptional disease control. The systemic and curative effects of the disease-control agents of this invention make a unique contribution to such combinations. For this reason, compositions containing another fungicide along with a compound of this case are often preferred. The systemic property of the compounds of this case is strikingly evident in the control of potato and tomato late blight disease on the foliage when treatments with the compounds are applied solely to the root system. Additional evidence comes from the curative action against established infections by the causal agent of late blight disease. The disease can be arrested even when treatments are delayed hours after plants have been inoculated.

Of the fungi causing diseases on agricultural crops, those classed as Phycomycetes are among the most virulent. The disorders caused by this group of fungi include late blight of tomatoes and potatoes, as well as downy mildew of grapes, cole crops, legumes, and cucurbits. Diseases caused by Phycomycetes are especially susceptible to control by the compounds of this invention.

The compounds of this invention provide protection from damage caused by certain fungi when applied to the proper locus by the methods described hereinafter and at a sufficient rate to exert the desired effect. They are especially suited for the protection of living plants by applying the compounds of this invention to the soil in which they are growing or in which they may subsequently be seeded or planted, to seeds, tubers, bulbs, or other plant reproductive parts prior to planting, as well as to foliage, stems, and/or fruit. Soil applications are made from dusts, granules, pellets, solutions, emulsions, or slurries.

Preferred rates for application of the compounds of this invention to soil in which plants are or will be growing range from 0.5 to 500 p.p.m. by weight of the soil in which the roots are or will be growing. More preferred use rates are in the range of 1 to 200 parts per million. The most preferred rates are in the range of 5 to 100 ppm. Preferred rates for application to seeds, tubers, bulbs, or other plant reproductive parts range from 0.5 to 100 g of active compound of this invention per kilo of planting material treated. More preferred rates are in the range of 1–75 g of active compound per kilo. The most preferred rates are in the range of 2–50 g per kilo. Applications of this type are made from dusts, slurries, emulsions, or solutions.

Preferred rates of application for the compounds of this invention to foliage, stems, and/or fruit of living plants range from 0.1 to 20 kilograms of active ingredient per hectare. More preferred rates are in the range of 0.2 to 10 kilos per hectare. The most preferred rates are in the range of 0.3 to 5 kilograms per hectare. The optimum amount within this range depends upon a number of variables which are well known to those skilled in the art of plant protection. The variables include, but are not limited to, the disease to be controlled, weather conditions expected, the type of crop, stage of development of the crop, and the interval between applications. Applications within the range given may need to be repeated one or many more times at intervals of 1 to 60 days. Applications are made from dusts, slurries, emulsions, or solutions.

The compositions of the invention can contain, in addition to the active ingredient of this invention, conventional insecticides, miticides, bactericides, nematicides, fungicides, or other agricultural chemicals such as fruit set agents, fruit thinning compounds, fertilizer ingredients and the like. Combinations with other fungicides, particularly maneb and chlorthalonil, are preferred. The additional agricultural chemicals are employed in mixtures or combinations in amounts ranging from one-tenth to twenty times that of the compound or compounds of this invention. The proper choice of amounts is readily made by one skilled in the art of protecting plants from pest depredations. The following are illustrative of the agricultural chemicals that may be included in compositions of the compounds of this invention or, additionally, that may be added to sprays containing one or more of the active compounds of this invention:

bis(dimethylthiocarbamoyl)disulfide or tetramethylthiuram disulfide (thiram);

metal salts of ethylenebisdithiocarbamic acid or propylenebisdithiocarbamic acids, e.g. manganese, zinc, iron and sodium salts (maneb or zineb);

n-dodecylguanidine acetate (dodine);

N-(trichloromethylthio)phthalimide (folpet);

N-[(trichloromethyl)thio]-4-cyclohexene-1,2-dicarboximide (captan);

cis-N-[(1,1,2,2-tetrachloroethyl)thio]-4-cyclohexene-1,2-dicarboximide (captafol);

2,4-dichloro-6-(o-chloroanilino)-$\alpha$-triazine ("Dyrene");

3,3'-ethylenebis(tetrahydro-4,6-dimethyl-2H-1,3,5-thiadiazine-2-thione), (milneb);

triphenyltin hydroxide (fentin hydroxide);

triphenyltin acetate (fentin acetate);

N'-dichlorofluoromethylthio-N,N-dimethyl-N'-phenylsulfamide (dichlofluanid);

tetrachloroisophthalonitrile (chlorthalonil);

tribasic copper sulfate;

fixed copper;

sulfur;

methyl 1-(butylcarbamoyl)-2-benzimidazolecarbamate (benomyl);

methyl 2-benzimidazolecarbamate;

1,2-bis(3-methoxycarbonyl-2-thioureido)benzene (methyl thiophanate).

The agricultural chemicals listed above are merely exemplary of the compounds which can be mixed with the active compounds of this invention and are not intended to any way limit the invention.

The use of pesticides in combination with a compound within the scope of this invention sometimes appears to greatly enhance the activity of the active compound of the invention. An unexpected degree of activity is sometimes seen when another pesticide is used along with the methods of this invention.

The useful compounds can be applied in a variety of formulations, including wettable powders, water-soluble powders, suspensions, emulsifiable concentrates, dusts, solutions, granules, pellets, etc. High strength compositions may also be prepared for use by local formulators in further processing.

These formulations include one or more compounds useful in this invention, and can include surface-active agents, solid or liquid diluents and other materials as required to produce the desired formulation.

The surface-active agents act as wetting, dispersing and emulsifying agents which assist dispersion of the active material in a spray, and improve wetting of waxy foliage and the like by the spray. Thus they aid in convenience, accuracy and effectiveness in use. The surfactants can include such anionic, non-ionic and cationic agents as have been used heretofore in pesticidal compositions of similar type. A detailed list of such agents may be found in "Detergents and Emulsifiers Annual", (John W. McCutcheon, Inc.). Addition of surfactants also prevents precipitation of large crystals of the active compounds on plant surfaces and improves penetration of the active compounds, thus increasing activity. Anionic and non-ionic surfactants are preferred. Such preferred surfactants include alkali and alkaline earth salts of alkylarylsulfonic acids, such as dodecylbenzenesulfonates and alkylnaphthalenesulfonates, dialkyl sodium sulfosuccinic esters, sodium lauryl sulfate, sodium N-methyl-N-oleoyltaurate, sodium dodecyldiphenyl ether disulfonic and the oleic acid ester of sodium isethionate. Other preferred surfactants include alkyl and alkylphenyl polyethylene glycol ethers, and their phosphate derivatives, polyoxyethylene derivatives of sorbitan fatty esters and long-chain alcohols and mercaptans, as well as polyoxyethylene esters of fatty acids. Film forming water-soluble polymers may be used in place of surfactants to improve activity. Humectants and oils chosen for low phytotoxicity also contribute to enhanced activity of the compositions of this invention. White oils having a viscosity of about 150 S.S.U. or higher are preferred.

Further information on formulation of the active compounds described above into the fungicial compositions of this invention can be found in J. B. Buchanan, U.S. Pat. No. 3,576,834 (4/27/71), R. R. Schaffer, U.S. Pat. No. 3,560,616 (2/2/71) and E. Somers, "Formulation," Chapter 6 in Torgeson, "Fungicides," Vol. I. Academic Press, New York, 1967.

The following examples further illustrate the invention. All parts and percentages are by weight.

EXAMPLE 1

A wettable powder formulation can be made and applied as follows:

| | Percent |
|---|---|
| 2-cyano-2-hydroxyiminoacetamide | 50 |
| sodium alkylnaphthalenesulfonate | 2 |
| low-viscosity methylcellulose | 2 |
| diatomaceous earth | 46 |

The ingredients are blended, coarsely hammer-milled and then air-milled to produce particles of active essentially all below 20 microns in diameter. The product is reblended before packaging.

All compounds of the invention may be formulated similarly.

This formulation is dispersed in water in an amount sufficient to provide a concentration of 400 ppm of the active compound of this invention. A portion of this is diluted to a concentration of 80 ppm. The dispersions are sprayed to the point of run-off on potted tomato plants and allowed to dry. Both treated and untreated plants are inoculated with a spore suspension of Phytophthora infestans and incubated for a day in a saturated humidity chamber. After five days of additional incubation in the greenhouse, all of the untreated tomatoes are dead because of late blight disease. The plants treated with the 80 ppm concentration have only an occasional confined lesion, whereas those treated with the 400 ppm concentration are completely healthy with no sign of disease. The other compounds of this invention can be substituted for 2-cyano-2-hydroxyiminoacetamide with like results. For example, 2-cyano-2-methoxyimino-N-methylcarbamoylacetamide, 2-acetoxyimino-2-cyano-N-methylacetamide, 2-cyano-N-ethylcarbamoyl-2-methoxyiminoacetamide, N-allylcarbamoyl-2-cyano-2-methoxyiminoacetamide, 2-cyano-2-methoxyimino-N-propylcarbamoylacetamide, 2-cyano-2-ethoxyimino-N-ethylcarbamoylacetamide, and the sodium or ammonium salt of 2-cyano-2-hydroxyiminoacetamide are particularly effective.

EXAMPLE 2

The formulation of Example 1 can be mixed in a spray tank with the fungicide benomyl. This formulation is diluted to a concentration of 500 ppm of the active ingredient. The benomyl in the mixture is at a concentration of 100 ppm. Sprays are applied to the point of run-off each week during the growing season to a cucumber field subject to infection by the downy mildew fungus (Pseudoperonospora cubensis), the powdery mildew fungus (Erysiphe chichoracearum), and the gummy stem blight fungus (Mycosphaerella citrullina). The plants which are sprayed with the mixture are healthy and bear a normal crop.

EXAMPLE 3

Potted greenhouse-grown tomato plants are inoculated by spraying them with a spore suspension of P. infestans. They are incubated in a saturated humidity chamber at 20°C for 8 hours. The infected tomato plants are removed from the incubation chamber long enough to spray them with various disease-control agents and combinations of these agents. The formulation of Example 1 is dispersed at a concentration of 400 ppm of the active ingredient. Similar dispersions are made of the commercial fungicides, maneb, captafol, metiram, and chlorothalonil. Additional treatments are made by mixing each of these dispersions of commercial fungicides with an equal quantity of the formulation of this example. This results in 200 ppm of each of the two component active ingredients. Six infected plants are sprayed with enough dispersion to have run-off of dry plants. After treatment, the plants are returned to the humidity chamber for a total of 24 hours. After an additional five days incubation in the greenhouse, the untreated plants are dead because of the late blight disease. Those plants treated with only the commercial fungicides are completely defoliated. The plants treated with the formulation of this invention have only a few restricted lesions. Most of the foliage is healthy. This is because of the unique curative action of the compounds of this invention. The best control is afforded by the mixtures of commercial fungicides and the compounds of this invention.

EXAMPLE 4

Potted greenhouse grown tomato plants are inoculated by spraying them with a spore suspension of P. infestans. They are incubated in a saturated humidity chamber at 20°C for 20 hrs. The infected tomato plants are removed from the incubation chamber long enough to spray them with various disease control agents. The compounds listed below are dispersed at a concentration of 80 ppm of the active ingredient. Three infected plants are sprayed with enough dispersion to have run-off of dry plants. After treatment, the plants are placed in a greenhouse for an additional 5 days incubation. The untreated plants are dead because of the late blight disease. The treated plants are rated for percent of foliage which is healthy (percent disease control). The curative action of the compounds of this invention is demonstrated in the following table.

| Compound | Percent Disease Control |
|---|---|
| 2-cyano-2-hydroxyiminoacetamide | 97 |
| 2-cyano-2-hydroxyiminoacetamide, | 80 |

-continued

| Compound | Percent Disease Control |
|---|---|
| sodium salt | |
| 2-cyano-2-hydroxyiminoacetamide, ammonium salt | 95 |
| 2-cyano-2-hydroxyiminoacetamide, iron salt | 93 |
| N-carbamoyl-2-cyano-2-methoxyimino-acetamide | 99 |
| 2-cyano-2-methoxyimino-N-methyl-carbamoylacetamide | 99 |
| 2-cyano-N-ethylcarbamoyl-2-methoxy-iminoacetamide | 100 |
| 2-cyano-2-methoxyimino-N-methyl-carbamoylacetamide | 100 |
| 2-cyano-2-methoxyimino-N-propyl-carbamoylacetamide | 100 |
| N-allylcarbamoyl-2-cyano-2-methoxy-iminoacetamide | 100 |
| Water treatment check | 0 |

EXAMPLE 5

A wettable powder formulation can be prepared as follows:

| | Percent |
|---|---|
| 2-cyano-2-methoxyimino-N-propylcarbamoylacetamide | 80 |
| sodium alkylnaphthalenesulfonate | 2 |
| sodium ligninsulfonate | 2 |
| synthetic amorphous silica | 3 |
| Kaolinite | 13 |

The ingredients are thoroughly blended, passed through a hammer-mill to produce an average particle size under 40 microns, reblended and sifted through a U.S.S. No. 50 sieve (0.3 mm openings) before packaging.

This formulation can be applied as follows: A potato field is selected in which there is a uniform but light infection of the late blight disease. The older foliage of each plant supports one or two sporulating Phytophthora infestans lesions. The plant damage at this point is slight, but the potential for disease spread is high. Plots are designated as five rows wide and 20 meters long. Treatments are assigned to various plots randomly through the field leaving much of the field untreated as buffers between treated plots. A series of treatments is selected for application immediately following weather conditions conducive to disease spread. Among those treatments is the formulation of this Example dispersed in water at a concentration of 300 ppm of active ingredient. Other treatments are a representation of commercially available fungicides such as maneb, captafol, and chlorothalonil, applied at their recommended use rate. In addition to these single compound applications, combinations of the formulation of this Example with each of the commercial fungicides are made at rates of ½of that used alone. Spray applications are made immediately after an overnight rain which had the potential of spreading the disease. After a week, the untreated foliage in this field is completely killed by the late blight disease. Those plots receiving treatments of commercial fungicides are severely diseased and are more than 80% defoliated. Those plots receiving the formulation of this Example are protected from the late blight disease and are only slightly defoliated. Those plots receiving the combination of the formulation of this invention plus a commercial fungicide are healthy and free of disease. The other compounds of this invention ma be substituted with like results.

EXAMPLE 6

An aqueous suspension can be prepared as follows:

| | Percent |
|---|---|
| 2-allyloxyimino-2-cyanoacetamide | 25 |
| hydrated attapulgite | 3 |
| crude calcium ligninsulfonate | 10 |
| disodium hydrogen phosphate | 0.5 |
| water | 61.5 |

The ingredients are ground together in a ball or roller mill until the solid particles have been reduced to diameters under 10 microns.

An established field of broccoli, in which downy mildew (Peronospora parasitica) is just appearing, is selected for treatment. Randomized plots throughout the field are sprayed with the formulation of this example dispersed in water at a concentration of 440 ppm active ingredient. Other plots are treated with commercial fungicides such as maneb, zineb, captofol, chlorothalonil and Bordeaux mixture. Spray applications are made on 7 to 10 day intervals, frequently a day after a rain or other natural infection period. At harvest time plants in the untreated plots are more than 50 percent infected and produce little or no yield. Plants sprayed with the commercial fungicides are about 20 percent infected with serious loss in yield. Plants treated with the formulation of this example are free of downy mildew and produce a normal yield.

EXAMPLE 7

An oil suspension can be prepared as follows and applied in a manner similar to example 5 with similar results.

| | Percent |
|---|---|
| 2-cyano-2-hydroxyiminoacetamide | 25 |
| polyoxyethylene sorbitol hexaoleate | 5 |
| highly aliphatic hydrocarbon oil | 70 |

The ingredients are ground together in a sand mill until the solid particles have been reduced to under about 5 microns. The resulting rather thick suspension may be applied directly, extended with oils, or emulsified in water.

EXAMPLE 8

An emulsifiable concentrate can be prepared and applied as follows:

| | Percent |
|---|---|
| 2-cyano-2-dodecyloxyiminoacetamide | 30 |
| isophorone | 65 |
| blend of oil-soluble sulfonates and polyoxyethylene ethers | 5 |

The ingredients are combined and stirred with gentle warming to speed solution. A fine screen filter is included in the packaging line to insure the absence of any undissolved matter in the final product.

EXAMPLE 9

A wettable powder can be prepared as follows:

|  | Percent |
|---|---|
| 2-cyano-N-ethylcarbamoyl-2-methoxyiminoacetamide | 80 |
| sodium dioctyl sulfosuccinate | 1 |
| sodium liguinsulfonate | 2 |
| attapulgite | 17 |

The ingredients are blended and passed through a hammer mill fitted with a coarse screen. After reblending, it is finely ground in a hammer mill and packaged.

Greenhouse grown grape plants are inoculated by spraying with a spore suspension of Plasmopara viticola, downy mildew. After 20 hours incubation in a 20° C saturated humidity chamber, six of the plants are sprayed to run-off with the above formulation dispersed in water to give 100 ppm active ingredient. Treatments with maneb at 2,000 ppm active are made on similar plants. After two weeks incubation in a greenhouse, the untreated plants and plants treated with maneb are severely infected with downy mildew (90 percent of the susceptible leaves are defoliated). Plants treated with the above formulation are free of disease, demonstrating the curative effect.

Tomato seedlings about 10 centimeters high are removed from the seed bed and immersed (roots only) in a solution containing 100 ppm of the active ingredient of the above formulation. Care is taken to avoid chemical contact with the stems or foliage. Roots are soaked 3 hours and then the plants are potted individually. Similar plants soaked in water are used as untreated checks. Five days after root treatment and transplanting the plants are inoculated with late blight by spraying the foliage with a spore suspension of P. infestans. The inoculated plants are incubated in a saturated humidity chamber for 24 hours and then incubated in the greenhouse. The plants receiving a root treatment at transplanting are healthy and free of late blight. The untreated check plants are killed by late blight infection. This demonstrates the systemic effect of the compounds of this invention.

EXAMPLE 10

A wettable powder can be prepared as follows:

| | Percent |
|---|---|
| 2-cyano-N-ethylcarbamoyl-2-methoxyiminoacetamide | 12 |
| manganous ethylene bis dithiocarbamate (maneb) | 78 |
| paraformaldehyde | 1 |
| sodium ligninsulfonate | 1 |
| zinc sulfate | 1 |
| sodium alkylnaphthalene sulfonate | 0.5 |
| methyl cellulose | 0.25 |
| kaolinite | 6.25 |

The ingredients are blended and finely ground in a hammer mill to produce a wettable powder practically all of which will pass through a U.S.S. No. 100 screen (0.149 mm openings).

The above formulation is dispersed in a spray tank to give a concentration of 200 ppm active 2-cyano-N-ethylcarbamoyl-2-methoxyiminoacetamide. The maneb is also an active component in this formulation. This mixture is compared with treatments of an equal amount of maneb (1,300 ppm) and maneb at double that concentration (2,600).

Tomato plants growing uniformly in a field are inoculated with a spore suspension of P. investans during a light rain which keeps the foliage wet overnight. The field is divided into plots so that each treatment can be replicated on four different plots. Treatments are applied as a spray to run off the day after the inoculation. Additional applications are made at 7 to 10 day intervals and in each case the sprays follow a natural or artificial (sprinkler) inoculaton period by one or two days. By the end of the test period the untreated plants ae more than 90% defoliated by late blight infections. The plants which are treated with maneb at 1,300 ppm are more than 50% defoliated and those treated with maneb at 2,600 ppm are about 30% defoliated. In contrast, the mixture in this formulation containing the active ingredient of this invention is so effective in curing established infections and preventing new infections that only an occasional lesion can be found in plots treated with this mixture.

The manganese ethylenebisdithiocarbamate in the above formulation can be replaced with similar amounts of commercial solid formulations of tetrachloroisophthalonitrile (chlorthalonil); N-(trichloromethylthio) phthalimide (folpet); 2,4-dichloro-6-(o-chloroanilino)-s-triazine; or cis-N-[(1,1,2,2-tetrachloroethyl)thio]-4-cyclohexene-1,2-dicarboximide (captafol).

EXAMPLE 11

A water soluble powder can be prepared as follows:

| | |
|---|---|
| 2-cyano-2-hydroxyiminoacetamide, sodium salt | 95.6% |
| sodium dioctylsulfosuccinate | 0.5% |
| methyl cellulose (65 ebs) | 1.0% |
| synthetic fine silica | 0.5% |
| sucrose | 2.4% |

The ingredients are blended and hammer-milled to produce a powder passing a U.S.S. No. 50 screen (0.3 mm opening). It contains the equivalent of 80% 2-cyano-2-hydroxyiminoacetamide. Other water soluble salts can be formulated similarly.

EXAMPLE 12

An aqueous solution can be made as follows:

| | |
|---|---|
| 2-cyano-2-hydroxyiminoacetamide, lithium salt | 22.9% |
| disodium hydrogen phosphate | 0.3% |
| water | 76.8% |

The ingredients are combined and stirred to produce a solution which contains the equivalent of 2 lbs. per gallon of 2-cyano-2-hydroxyiminoacetamide.

EXAMPLE 13

A wettable powder formulation can be made as follows:

| | |
|---|---|
| 2-cyano-2-methoxyimino-N-methyl carbamoylacetamide | 75% |
| dodecylphenol polyethylene glycol ether | 2% |
| sodium ligninsulfonate | 4% |
| sodium silicoaluminate | 5% |
| montmorillonite | 14% |

The liquid surfactant is sprayed upon the solid ingredients while blending. The mixture is then ground in a hammer-mill to produce a product essentially all finer than 100 microns which is reblended and packaged.

EXAMPLE 14

A wettable powder formulation can be prepared as follows:

| | |
|---|---|
| 2-cyano-2-methoxyimino-N-propylcarbamoyl-acetamide | 75% |
| sodium alkylnaphthalene sulfonate | 2% |
| oleic acid ester of sodium isethionate | 2% |
| diatomite | 21% |

The ingredients are blended, hammer-milled, and then air-milled to produce an average particle size under 25μ. After reblending and sifting through a U.S.S. No. 50 sieve (0.3 mm opening) the product is packaged.

EXAMPLE 15

A dust can be prepared as follows:

| | |
|---|---|
| N-allylcarbamoyl-2-cyano-2-methoxy-iminoacetamide | 5% |
| attapulgite | 10% |
| pyrophyllite | 85% |

The active ingredient and attapulgite are hammer-milled to provide particles of active substantially below 50 microns. This mixture is then blended with the pyrophyllite to provide the final formulation.

EXAMPLE 16

| | |
|---|---|
| 2-cyano-2-ethoxyimino-N-ethylcarbamoyl-acetamide | 10% |
| talc | 90% |

The ingredients are blended and passed through a hammer mill to produce particles of active ingredient substantially below 50μ.

I claim:

1. A method for inhibiting fungus diseases in plants consisting essentially of applying to the plants a compound of the formula

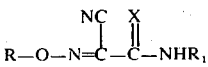

wherein
R is hydrogen; alkyl of 1 to 13 carbon atoms; alkyl of 1 to 13 carbon atoms substituted with alkoxycarbonyl of 2 to 4 carbon atoms, acyl of 2 to 4 carbon atoms, cyano, hydroxyl, acyloxy of 2 to 4 carbon atoms,

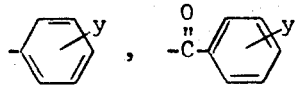

or

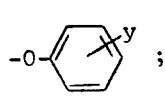

alkenyl of 3 to 6 carbon atoms; cycloalkyl of 5 to 7 carbon atoms; acyl of 1 to 4 carbon atoms;

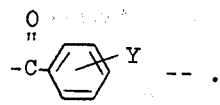

or a cation selected from the group consisting of lithium sodium, potassium, calcium, and $NR_2R_3R_4R_5$;
  y is hydrogen, chlorine, fluorine, bromine, methyl or cyano;
  $R_2$ is hydrogen, alkyl of 1 to 4 carbon atoms, 2-hydroxyethyl or alkoxyethyl of 3 to 4 carbon atoms;
  $R_3$ is hydrogen, alkyl of 1 to 4 carbon atoms, 2-hydroxyethyl or alkoxyethyl of 3 to 4 carbon atoms
  $R_4$ is hydrogen, alkyl of 1 to 4 carbon atoms, 2-hydroxyethyl, or alkoxyethyl of 3 to 4 carbon atoms;
  $R_5$ is hydrogen, alkyl of 1 to 12 carbon atoms, 2-hydroxyethyl, alkoxyethyl of 3 to 4 carbon atoms or benzyl;
  $R_1$ is hydrogen,

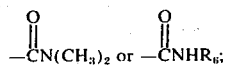

$R_6$ is hydrogen, alkyl of 1 to 4 carbon atoms or allyl;
X is oxygen or sulfur with the proviso that
1. when $R_1$ is

or when X is sulfur, R is methyl;
2. when R is a cation, $R_1$ is hydrogen;
3. when R is substituted alkyl, the total number of carbon atoms is R is less than 14 in an amount sufficient to inhibit the fungus disease.

2. The method of claim 1 wherein
$R_6$ is hydrogen or alkyl of 1 to 4 carbon atoms provided that when R is alkyl of 2 to 6 carbon atoms or cycloalkyl of 5 to 7 carbon atoms, $R_1$ is

3. The method of claim 1 wherein
$R_1$ is

R is alkyl of 1 to 13 carbon atoms; alkyl of 1 to 13 carbon atoms substituted with alkoxycarbonyl of 2 to 4 carbon atoms, acyl of 2 to 4 carbon atoms, hydroxyl, cyano, acyloxy of 2 to 4 carbon atoms,

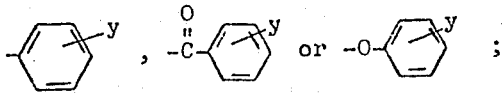

alkenyl of 3 to 6 carbon atoms; cycloalkyl of 5 to 7 carbon atoms; O,O-dialkyl thiophosphoryl of 2 to 4 carbon atoms; acyl of 1 to 4 carbon atoms or

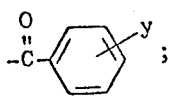

Y is hydrogen, chlorine, fluorine, bromine, methyl or cyano; and $R_6$ is hydrogen, alkyl of 1 to 4 carbon atoms or allyl provided that the total number of carbon atoms in the substituent R is less than 14.

4. The method of claim 3 wherein $R_6$ is hydrogen or alkyl or 1 to 4 carbon atoms.

5. The method of claim 2 wherein
$R_1$ is hydrogen
X is oxygen; and
R is hydrogen, methyl or a cation.

6. The method of claim 3 wherein
X is oxygen;
R is alkyl of 1 to 4 carbon atoms; and
$R_6$ is hydrogen, alkyl of 1 to 4 carbon atoms or allyl.

7. The method of claim 5 wherein the compound is 2-cyano-2-hydroxyiminoacetamide.

8. The method of claim 5 wherein the compound is 2-cyano-2-hydroxyiminoacetamide, sodium salt.

9. The method of claim 5 wherein the compound is 2-cyano-2-hydroxyiminoacetamide, ammonium salt.

10. The method of claim 6 wherein the compound is N-carbamoyl-2-cyano-2-methoxyiminoacetamide.

11. The method of claim 6 wherein the compound is 2-cyano-2-methoxyimino-N-methylcarbamoylacetamide.

12. The method of claim 6 wherein the compound is 2-cyano-N-ethylcarbamoyl-2-methoxyiminoacetamide.

13. The method of claim 6 wherein the compound is 2-cyano-2-ethoxyimino-N-ethylcarbamoylacetamide.

14. The method of claim 6 wherein the compound is N-allylcarbamoyl-2-cyano-2-methoxyiminoacetamide.

15. The method of claim 6 wherein the compound is 2-cyano-2-methoxyimino-N-propylcarbamoylacetamide.

16. A composition useful for inhibiting fungus diseases in plants consisting of an inert diluent and an amount of a compound sufficient to inhibit the fungus disease, said compound having the formula:

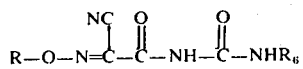

wherein
R is alkyl of 1 to 13 carbon atoms; alkyl of 1 to 13 carbon atoms substituted with alkoxycarbonyl of 2 to 4 carbon atoms, acyl of 2 to 4 carbon atoms, hydroxyl, cyano, acyloxy of 2 to 4 carbon atoms,

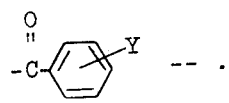

alkenyl, of 3 to 6 carbon atoms; cycloalkyl of 5 to 7 carbon atoms; acyl of 1 to 4 carbon atoms or Y is hydrogen, chlorine, fluorine, bromine, methyl or cyano; and $R_6$ is hydrogen, alkyl of 1 to 4 carbon atoms or allyl provided that the total number of carbon atoms in the substituent R is less than 14.

17. A composition of claim 16 wherein $R_6$ is hydrogen or alkyl of 1 to 4 carbon atoms.

18. A composition of claim 16 wherein R is alkyl of 1 to 4 carbon atoms and $R_6$ is alkyl of 1 to 4 carbon atoms or allyl.

19. A composition of claim 18 wherein the compound is 2-cyano-2-methoxyimino-N-methylcarbamoylacetamide.

20. A composition of claim 18 wherein the compound is 2-cyano-N-ethylcarbamoyl-2-methoxyiminoacetamide.

21. A composition of claim 18 wherein the compound is 2-cyano-2-ethoxyimino-N-ethylcarbamoylacetamide.

22. A composition of claim 18 wherein the compound is N-allylcarbamoyl-2-cyano-2-methoxyiminoacetamide.

23. A composition of claim 18 wherein the compound is 2-cyano-2-methoxyimino-N-propylcarbamoylacetamide.

24. A composition of claim 18 wherein the compound is N-carbamoyl-2-cyano-2-methoxyiminoacetamide.

25. A fungicidal composition consisting essentially of an amount of 2-cyano-N-ethylcarbamoyl-2-methoxyiminoacetamide sufficient to inhibit fungus diseases in plants and a fungicidally
effective amount of a fungicide selected from the group consistion of
bis(dimethylthiocarbamoyl)disulfide
tetramethylthiuran disulfide
manganese ethylenebisdithiocarbamate
zinc ethylenebisdithiocarbamate
iron ethylenebisdithiocarbamate
sodium ethylenebisdithiocarbamate
manganese propylenebisdithiocarbamate
zinc propylenebisdithiocarbamate
iron propylenebisdithiocarbamate
sodium propylenebisdithiocarbamate
n-dodecylguanidine acetate
N-(trichloromethylthio)phthalimide
N-[(trichloromethyl)thio]-3-cyclohexene-1,2-dicarboximide
cis-N-[(1,1,2,2-tetrachloroethyl)thio]-4-cyclohexene-1,2-dicarboximide
2,4-dichloro-6-(o-chloroanilino)-α-triazine
3,3'-ethylenebis(tetrahydro-4,6-dimethyl-2H-1,3,5-thiadiazine-2-thione)
triphenyl tin hydroxide
triphenyl tin acetate
N'-dichlorofluoromethylthio-N,N-dimethyl-N'-phenylsulfamide
tetrachloroisophthalonitrile
tribasic copper sulfate
fixed copper
sulfur
methyl 1-(butylcarbamoyl)-2-benzimidazolecarbamate
methyl 2-benzimidazolecarbamate, and 1,2-bis(3-methoxycarbonyl-2-thioureido)benzene.

26. A fungicidal composition of claim 25 consisting essentially of a fungicidally effective amount of manganese ethylenebisdithiocarbamate and 2-cyano-N-ethylcarbamoyl-2-methoxyiminoacetamide.

27. A fungicidal composition of claim 25 consisting essentially of a fungicidally effective amount of chloroisophthalonitrile and 2-cyano-N-ethylcarbamoyl-2-methoxyiminoacetamide.

* * * * *